United States Patent
Melsheimer et al.

(10) Patent No.: US 9,408,600 B2
(45) Date of Patent: Aug. 9, 2016

(54) RELEASABLE SUTURE CLAMP AND SUTURE ANCHOR ASSEMBLY INCLUDING SAME

(71) Applicants: Jeffry S. Melsheimer, Springville, IN (US); Kristyn Gadlage, Beech Grove, IN (US)

(72) Inventors: Jeffry S. Melsheimer, Springville, IN (US); Kristyn Gadlage, Beech Grove, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 618 days.

(21) Appl. No.: 13/761,571

(22) Filed: Feb. 7, 2013

(65) Prior Publication Data

US 2013/0204297 A1 Aug. 8, 2013

Related U.S. Application Data

(60) Provisional application No. 61/595,792, filed on Feb. 7, 2012.

(51) Int. Cl.
*A61B 17/04* (2006.01)
*A61B 17/06* (2006.01)

(52) U.S. Cl.
CPC ......... *A61B 17/0401* (2013.01); *A61B 17/0487* (2013.01); *A61B 17/06114* (2013.01); *A61B 2017/0417* (2013.01); *A61B 2017/0488* (2013.01); *A61B 2017/0496* (2013.01); *A61B 2017/06052* (2013.01)

(58) Field of Classification Search
CPC ........... A61B 17/0401; A61B 17/0487; A61B 17/06114; A61B 19/0256; A61B 2017/0417; A61B 2017/0488; A61B 2017/0496; A61B 2017/06052
See application file for complete search history.

(56) References Cited

U.S. PATENT DOCUMENTS

| | | | |
|---|---|---|---|
| 6,432,123 B2 * | 8/2002 | Schwartz | .......................... 289/2 |
| 6,716,243 B1 | 4/2004 | Colvin et al. | |
| 7,806,910 B2 | 10/2010 | Anderson | |
| 7,862,584 B2 | 1/2011 | Lyons et al. | |
| 2006/0265012 A1 * | 11/2006 | Anderson | .......... A61B 17/0487 606/232 |
| 2013/0158600 A1 * | 6/2013 | Conklin | ............. A61B 17/0401 606/232 |
| 2013/0211427 A1 * | 8/2013 | Castell Gomez | .. A61B 17/0401 606/144 |

* cited by examiner

*Primary Examiner* — Tuan V Nguyen
*Assistant Examiner* — Kevin Everage
(74) *Attorney, Agent, or Firm* — Liell & McNeil

(57) ABSTRACT

A suture anchor assembly includes a length of suture having an anchor attached to an end thereof. A releasable suture clamp is disposed in a clamped configuration about the suture. The releasable suture clamp includes a plurality of independent stackable components rotatable about a common axis, which is transverse to opposing faces of the stackable components. Each of the stackable components has a first opening passing through the opposing faces, spaced from the common axis, and sized for receiving the suture therethrough. The releasable suture clamp has an unclamped configuration in which the first openings are aligned relative to an alignment axis and the clamped configuration in which the first openings are misaligned relative to the alignment axis, wherein the alignment axis is parallel to the common axis.

20 Claims, 3 Drawing Sheets

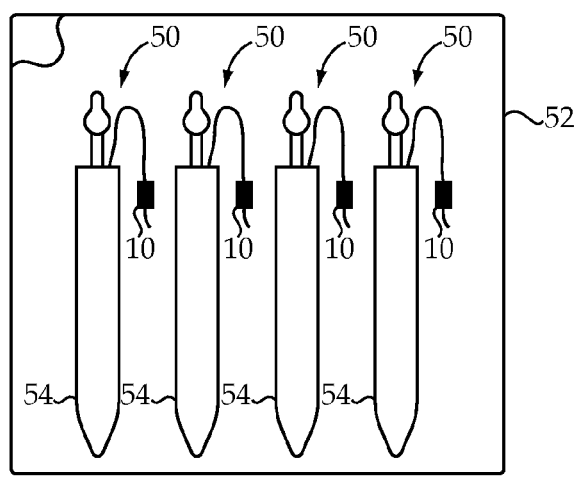
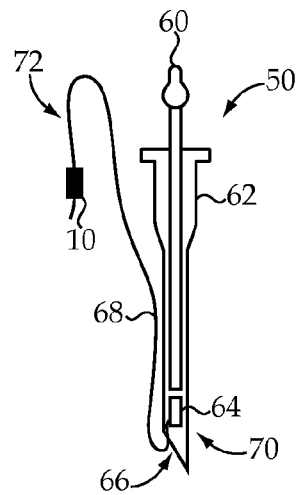
Figure 6    Figure 7
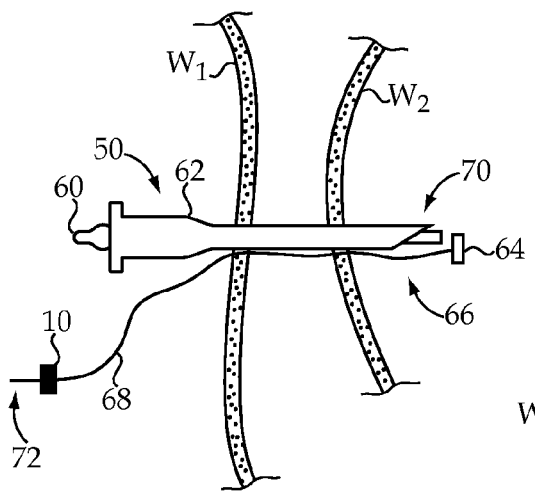
Figure 8
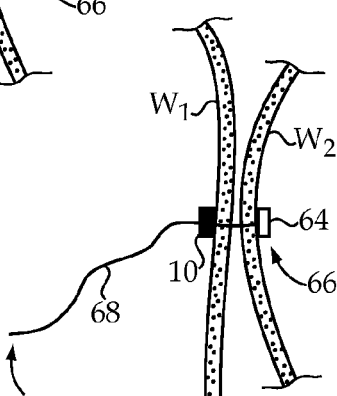
Figure 9
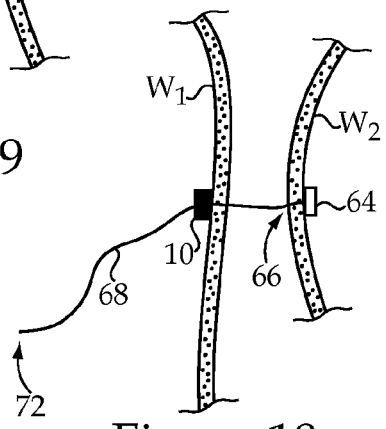
Figure 10

RELEASABLE SUTURE CLAMP AND SUTURE ANCHOR ASSEMBLY INCLUDING SAME

RELATION TO OTHER PATENT APPLICATION

This application claims priority to provisional patent application 61/595,792, filed Feb. 7, 2012, with the same title.

TECHNICAL FIELD

The present disclosure relates generally to a releasable suture clamp and a suture anchor assembly including same, and more particularly to a releasable suture clamp that includes a plurality of independent stackable components rotatable about a common axis to move the releasable suture clamp between clamped and unclamped configurations.

BACKGROUND

Sutures are commonly used in medical procedures to sew tissue together in order to close tissue openings, cuts, or incisions during or after the medical procedure. Sutures are also used, in conjunction with anchors or other similar devices, to achieve or maintain traction, or other positioning of tissues or organs, during medical procedures. According to any of these uses and others, sutures are typically looped through the tissue and the one or more free ends knotted to maintain a desired position or tension of the suture. More specifically, a clinician may manually tie together a suture pair or knot a free end of a single suture to secure the appropriate positioning. According to embodiments where the suture is used to maintain traction, tension in the suture between the anchor and the knot tied adjacent the patient's skin ultimately provides the desired traction.

Although knotting sutures may prove effective for certain procedures, there are a number of disadvantages of knotting sutures to secure tissues to one another and/or maintain a desired tension. For example, knot tying may require a considerable amount of time and may require a certain degree of dexterity. Further, knots may permanently fix a suture in place and, thus, may not be removed or adjusted once in place without removing the entire suture. Thus, although an additional knot may be created to increase suture tension, decreasing suture tension may require abandoning the previous suture and using another suture that may be knotted at the appropriate tension.

U.S. Pat. No. 7,806,910 to Anderson teaches a suture clip comprising a plurality of flexible elements positioned together in a row. Specifically, first ends of the elements, which are bonded together at second ends thereof, are movable about living hinges and configured such that a tool may be used to urge the first ends of at least a portion of the flexible elements inward to define a slot between the first ends of the elements. A suture may be received within the slot, while the tool is actuating the flexible elements, and may later be held by the clip when the flexible elements are moved apart such that a tortuous path through the first ends of the elements is defined. The suture clip taught by Anderson, which appears to require a tool for actuation, is particularly suited for internal suturing, as described in the disclosure.

The present disclosure is directed toward one or more of the problems or issues set forth above.

SUMMARY OF THE DISCLOSURE

In one aspect, a suture anchor assembly includes a length of suture having an anchor attached to an end thereof. A releasable suture clamp is disposed in a clamped configuration about the suture. The releasable suture clamp includes a plurality of independent stackable components rotatable about a common axis, which is transverse to opposing faces of the stackable components. Each of the stackable components has a first opening passing through the opposing faces, spaced from the common axis, and sized for receiving the suture therethrough. The releasable suture clamp has an unclamped configuration in which the first openings are aligned relative to an alignment axis and the clamped configuration in which the first openings are misaligned relative to the alignment axis, wherein the alignment axis is parallel to the common axis.

In another aspect, a releasable suture clamp includes a plurality of independent stackable components rotatable about a common axis, which is transverse to opposing faces of the stackable components. Each of the stackable components has a first opening passing through the opposing faces, spaced from the common axis, and sized for receiving a suture therethrough. The releasable suture clamp has an unclamped configuration in which the first openings are aligned relative to an alignment axis, which is parallel to the common axis, and a clamped configuration in which the first openings are misaligned relative to the alignment axis.

In another aspect, a method of clamping a suture with a releasable suture clamp includes a step of moving the releasable suture clamp from a clamped configuration to an unclamped configuration by rotating a plurality of independent stackable components of the releasable suture clamp about a common axis such that first openings are aligned relative to an alignment axis and define a linear path. The suture is received through the first openings along the linear path. The releasable suture clamp is then returned from the unclamped configuration to the clamped configuration by rotating the stackable components about the common axis such that the first openings are misaligned relative to the alignment axis and define a serpentine path. Movement of the suture relative to the suture clamp is restricted by gripping the suture with edges defining the first openings and surfaces of the stackable components defining the serpentine path.

BRIEF DESCRIPTION OF THE DRAWINGS

FIG. 6 is a plan view of a sterilized package containing a plurality of suture anchor assemblies including releasable suture clamps, according to another aspect of the present disclosure;

FIG. 7 is a side sectioned view of a suture anchor assembly of FIG. 6, shown with a blunt end holder removed;

FIG. 8 is a side diagrammatic view of an abdomen wall and stomach of a patient at one stage of a percutaneous gastrostomy procedure, which illustrates an exemplary use of the suture anchor assembly of FIG. 7;

FIG. 9 is a side diagrammatic view of the abdomen wall and stomach at another stage of the gastrostomy procedure; and FIG. 10 is a side diagrammatic view of the abdomen wall and stomach at another stage of the gastrostomy procedure.

DETAILED DESCRIPTION

Figure 1:
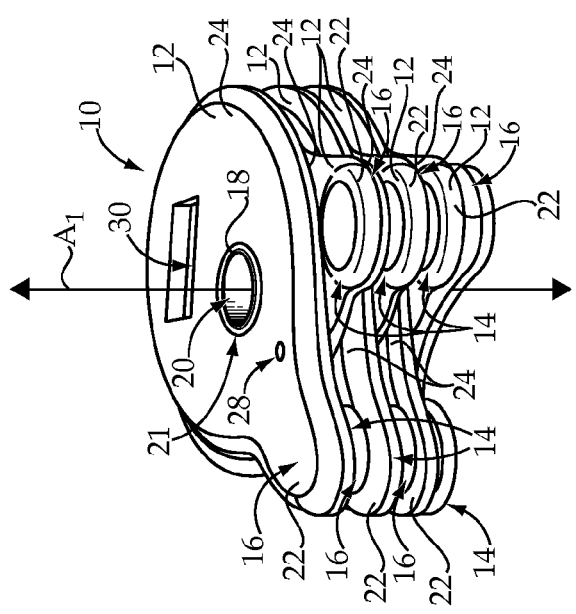
FIG. 1 is a perspective view of a releasable suture clamp, shown in a clamped configuration, according to one embodiment of the present disclosure.

Referring to FIG. 1, there is shown a releasable suture clamp 10 according to one embodiment of the present disclosure. The releasable suture clamp 10 generally includes a plurality of independent stackable components 12 rotatable about a common axis $A_1$. According to the exemplary embodiment, the common axis $A_1$ is transverse to opposing faces 14 and 16 of the stackable components 12. As shown, and as will be discussed in greater detail below, the stackable components 12 may be stacked such that alternate components 12 have substantially similar orientations and adjacent, or abutting, components 12 have inverted orientations. In particular, the components 12 may be stacked, or arranged, such that faces 14 of adjacent components 12 contact one another and faces 16 of adjacent components 12 contact one another. Further, adjacent components 12 of the releasable suture clamp 10 may also be rotated, or skewed, relative to the common axis $A_1$ for reasons described in greater detail below.

According to the exemplary embodiment, a retaining pin 18 may be secured within openings 20 passing through the opposing faces 14 and 16 of each of the stackable components 12 to define the common axis $A_1$. The retaining pin 18 may function to hold the stackable components 12 in the stacked configuration that is shown and also allow relative movement of each of the components 12 about the common axis $A_1$. Thus, particular embodiments of the retaining pin 18 may vary, as long as the recited functionality is provided. According to a specific example, the retaining pin 18, which may include any number of components, may have ends that define retaining flanges 21 sized and configured to maintain the stacked configuration of the components 12.

Figure 2:
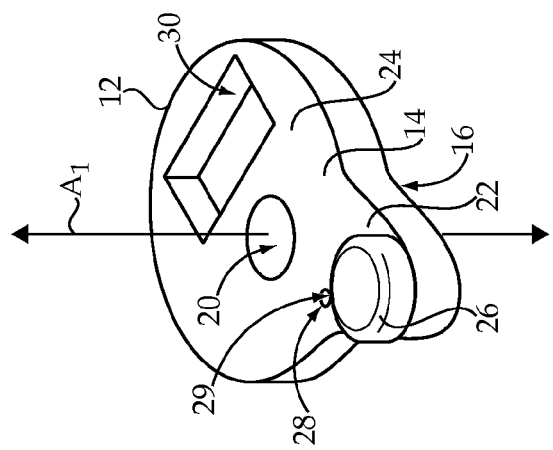
FIG. 2 is a perspective view of one of a plurality of independent stackable components of the releasable suture clamp of FIG. 1.

Referring also to FIG. 2, each of the stackable components 12 may include a lobe 22 extending from an otherwise substantially disc-shaped body 24. Although the shape and configuration of the stackable components 12 may vary, the lobes 22 may function to enhance the ability of a clinician to grip and rotate the components 12 of the clamp 10. As is best shown in FIG. 2, a projection 26 may extend transversely from each face 14 and, more particularly, from each lobe 22. The projections 26, which may be multi-functional, will be discussed in greater detail below.

Each of the stackable components 12 also includes an opening 28, defined by edge 29, passing through the opposing faces 14 and 16, spaced from the common axis $A_1$, and sized for receiving at least one suture (not shown) therethrough. An additional opening or, more specifically, a slot 30 may also be provided through each component 12 for receiving a spring member or other tensioning device. The opening 28 and slot 30, both of which will be discussed below in greater detail, are positioned along the faces 14 and 16 such that, when the components 12 are stacked as described above, the openings 28 and slots 30 of adjacent or abutting components 12 may be offset from one another, while openings 20 remain substantially aligned. Movement of the releasable suture clamp 10 between clamped and unclamped configurations, as will be described below, rotate the components about the common axis $A_1$ such that the openings 28 and slots 30 of adjacent components 12 move relative to one another.

Figure 3:
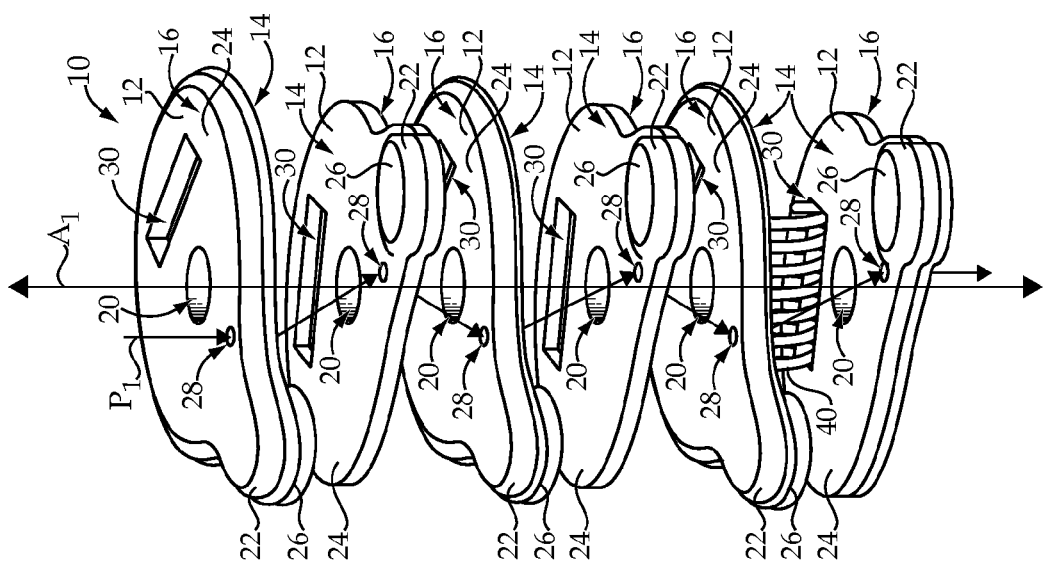
FIG. 3 is an exploded view of the releasable suture clamp of FIG. 1, shown in the clamped configuration.

Turning now to FIG. 3, an exploded view of the releasable suture clamp 10 is shown with the retaining pin 18 removed. The depicted configuration of the releasable suture clamp 10, which is a clamped configuration of the clamp 10, may be a biased, or resting, configuration of the clamp 10. Specifically, a spring member 40, which may be received within slots 30 of each of the stackable components 12, may maintain, or assist in maintaining, the clamped configuration of the releasable suture clamp 10. In particular, the slots 30 may be positioned and sized such that, when the stackable components 12 are positioned as described above and shown in FIG. 3, the slots 30 of adjacent or abutting components 12 overlap an amount sufficient to house the spring member 40 in a relaxed or untensioned state.

Accordingly, the spring member 40 assists in maintaining the clamped configuration, in which the suture openings 28 are misaligned to define a serpentine path $P_1$. "Misaligned," as used herein, means not aligned along a linear path. Although overlap of the suture openings 28 is contemplated, the suture openings 28 of adjacent or abutting components 12 may preferably be free of any overlap in the clamped configuration. The amount of overlap, if any, along with the number of stackable components 12 used, materials selected, and surface finishes provided, are all exemplary design considerations and should be selected to provide a desired clamping force on a suture in the clamped configuration of the clamp 10.

Figure 4:
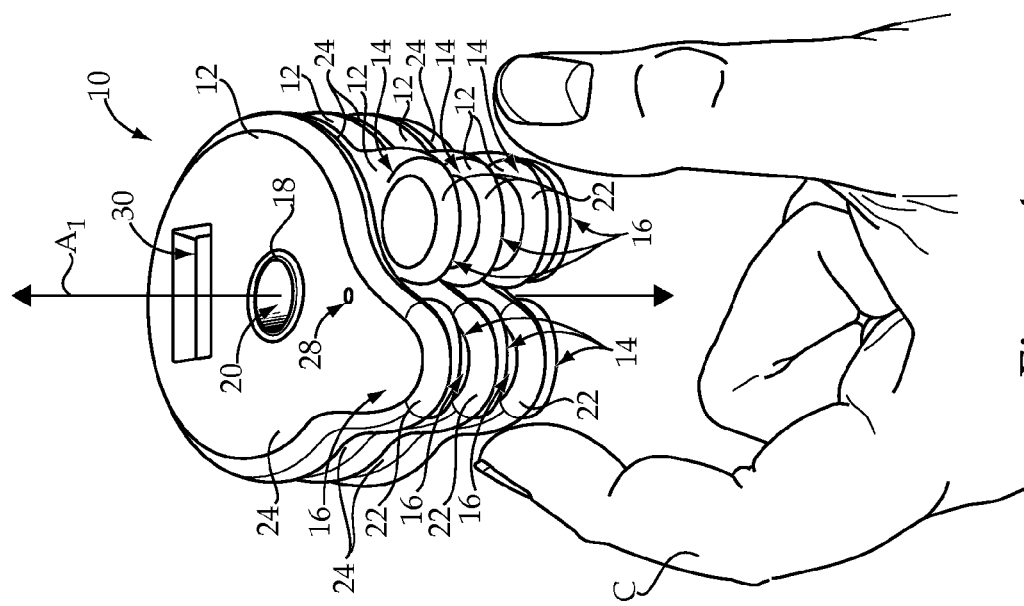
FIG. 4 is a perspective view of the releasable suture clamp of FIG. 1, shown in an unclamped configuration.

To move the releasable suture clamp 10 from the clamped configuration of FIGS. 1 and 3 to an unclamped configuration, the lobes 22, including projections 26, may be moved closer together. Specifically, as shown in FIG. 4, a clinician C may use a forefinger and thumb to grip the lobes 22, and possibly the projections 26, to rotate the stackable components 12 about the common axis $A_1$. More specifically, the stackable components 12 may be rotated about the retaining pin 18 (FIG. 1) that is secured within openings 20. By rotating the stackable components 12 in such a manner, the spring member 40 is tensioned by decreasing the overlap amount of the slots 30 of adjacent or abutting components 12, and the releasable suture clamp 10 may be moved against the biasing force of spring member 40 into the unclamped configuration. According to some embodiments, the slots 30 may be curved to accommodate compression of the spring member 40 without binding. Referring also to the exploded view of the unclamped configuration shown in FIG. 5, the suture openings 28 of adjacent or abutting components 12 are substantially aligned along an alignment axis $A_2$ to define a linear path $P_2$. The alignment axis $A_2$, as shown, is parallel to the common axis $A_1$.

Figure 5:
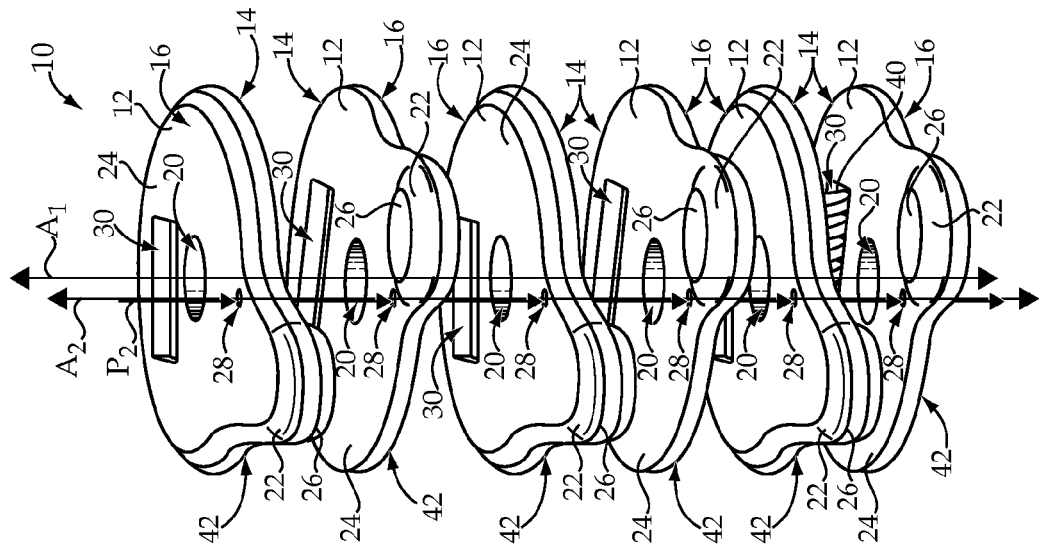
FIG. 5 is an exploded view of the releasable suture clamp of FIG. 4, shown in the unclamped configuration.

As should be appreciated, the lobes 22 and projections 26 may also function to restrict movement of the releasable suture clamp 10 beyond a movement range defined by the clamped configuration (FIGS. 1 and 3) and the unclamped configuration (FIGS. 4 and 5). Specifically, the projections 26 may be restricted by edges 42 of adjacent or abutting components 12 from movement beyond the described movement range. Thus, the lobes 22 of adjacent or abutting components 12 may be restricted from moving farther apart than the positions shown in FIGS. 1 and 3, and may be restricted from moving closer together than the positions shown in FIGS. 4 and 5.

According to some embodiments, an end plate (not shown) may be provided on each end of the releasable suture clamp 10 and positioned over the corresponding slot 30 to assist in retaining the spring member 40 within the slots 30. The end plates may be integral with or attached to the retaining pin 18.

Turning now to FIG. 6, an exemplary commercial embodiment according to the present disclosure is shown. Specifically, a plurality of suture anchor assemblies 50, including releasable suture clamps 10, are shown positioned in a sterilized package 52. Each of the suture anchor assemblies 50, including the suture assembly components described below, may be protectively housed in a blunt end holder 54 to cover the relatively sharp needle tip housed therein. The sterilized package 52 may, for example, contain four suture anchor assemblies 50, as shown; however, each suture anchor assembly 50 could be individually packaged, or packaged in different multiples without departing from the scope of the present disclosure. Further, it should be noted that the sterilized package 52 may include additional components, such as, for example, an antiseptic, drape, anesthetic, syringe, forceps, scalpel, gauze, scissors, etc. One skilled in the art will appreciate that the sterilized package 52 may include a variety of components that may differ, depending on the particular medical procedure for which the package 52 is provided.

FIG. 7 shows a sectioned view of one of the suture anchor assemblies 50 with the blunt end holder 54 removed to reveal a pusher 60 that is slidably received within a needle 62. An anchor 64, attached to a distal end 66 of a length of suture 68, is received within a distal end 70 of the needle 62, as shown. The suture 68 extends outside of the needle 62 and has a releasable suture clamp 10 disposed in a clamped configuration (shown in FIGS. 1 and 3) about a proximal end 72 of the suture 68. In the unclamped configuration (shown in FIGS. 4 and 5), the releasable suture clamp 10 may slide along the length of the suture 68. As should be appreciated, it may be desirable to provide suture anchor assemblies 50, or other similar assemblies, with pre-threaded releasable suture clamps 10 that do not require initial threading during the procedure.

INDUSTRIAL APPLICABILITY

The present disclosure is generally applicable to medical devices for use in medical procedures involving suturing. More specifically, the present disclosure is applicable to devices or components for retaining sutures at a desired positions and/or tensions. Yet further, the present disclosure may be specifically applicable to suture retaining devices or components that maintain a desired tension of the suture without the use of conventional knot tying.

Referring generally to FIGS. 1-10, a portion of an exemplary medical procedure is shown to illustrate an exemplary use of the suture anchor assembly 50 and, more particularly, the releasable suture clamp 10 of the present disclosure. Specifically, according to an exemplary percutaneous gastrostomy procedure, a clinician may insert a feeding tube (not shown) through a small incision in the abdominal wall $W_1$ of a patient and into the stomach $W_2$. In order to perform such a procedure, the clinician may begin by opening sterilized package 52 and removing, among other items, one of the suture anchor assemblies 50. Thereafter, the blunt end holder 54 may be removed to reveal the sharp end of needle 62. The clinician may then pierce through the abdominal wall $W_1$ into the stomach $W_2$ of the patient with needle 62. After confirming proper placement, the anchor 64 is then deployed in the stomach $W_2$ by advancing pusher 60 through the needle 62, as shown in FIG. 8. Next, the needle 62 is withdrawn from the patient leaving a segment of suture 68 extending from outside the patient into the stomach $W_2$, with the distal end 66 attached to the anchor 64. The releasable suture clamp 10 is disposed about the proximal end 72 of the suture 68, in the clamped configuration, as shown.

Next, the stomach $W_2$ of the patient is pulled against the abdominal wall $W_1$ by tensioning the suture 68 so that anchor 64 bears against the wall of the patient's stomach $W_2$ as shown in FIG. 9. Next, the clinician may move the releasable suture clamp 10 from the biased clamped configuration of FIGS. 1 and 3 and into the unclamped configuration of FIGS. 4 and 5 by squeezing the lobes 22 and projections 26 closer together and rotating the stackable components 12 inward about the common axis $A_1$. In the unclamped configuration, the suture openings 28 of adjacent or abutting components 12 are substantially aligned along an alignment axis $A_2$ to define a linear path $P_2$. The releasable suture clamp 10 may then be slid along the suture 68 and positioned adjacent the patient's skin, as shown in FIG. 9.

Once the releasable suture clamp 10 is moved to the desired position, the clamp 10 may be moved from the unclamped configuration and returned to the clamped configuration to maintain the desired position and/or tension of the suture 68. Specifically, the clinician may release a grip on the lobes 22 and/or projections 26 to allow the spring member 40 to increase the overlap amount of the slots 30 of adjacent or abutting components 12 and move the lobes 22 and projections 26 of adjacent or abutting components 12 farther apart. More specifically, the stackable components 12 may be rotated outward about the common axis $A_1$ such that the suture openings 28 of adjacent or abutting components 12 are misaligned relative to the alignment axis $A_2$ and define a serpentine path $P_1$.

Movement of the suture 68 is restricted relative to the releasable suture clamp 10 by gripping the suture 68 with edges 29 defining the suture openings 28 and surfaces 14 and 16 of the components 12 defining the serpentine path $P_1$. Thus, the releasable suture clamp 10, in the clamped configuration, maintains a first tension or position of the suture 68, as shown. Specifically, the tension in the suture 68 between the anchor 64 and releasable suture clamp 10 positioned adjacent the patient's skin ultimately provides the desired traction of the stomach $W_2$. As should be appreciated, this procedure may be twice more repeated until forming a triangular pattern on the patient's abdomen for surrounding a central location for placement of a feeding tube in a known manner.

If required, or desired, the clinician may readily reposition the suture 68 at a second tension, which is different than the first tension, using the releasable suture clamp 10. Specifically, the clinician may again grip the lobes 22 of the stackable components 12 to move the lobes 22 closer together and rotate the components 12 about the common axis $A_1$, against the bias of spring member 40, until the projections 26 restrict further movement of the components 12. In this unclamped configuration of the releasable suture clamp 10, the suture openings 28 align to define the linear path $P_2$. The clamp 10 may then be slid along the suture 68, which is substantially aligned along the linear path $P_2$, and away from the patient such that the tension of the suture 68 may be loosened, as shown. To increase the tension, the releasable suture clamp 10 may be moved in the opposite direction, i.e., toward the patient.

After the appropriate tension is achieved, the releasable suture clamp 10 may be returned to the clamped configuration to maintain the adjusted tension of the suture 68. Specifically, the lobes 22 may be released and allowed to move farther apart. As the stackable components 12 are rotated outward about the common axis $A_1$, using the biasing force of spring member 40, the suture openings 28 of adjacent or abutting components 12 become misaligned relative to the alignment axis $A_2$ and define the serpentine path $P_1$, which maintains the second tension or position of the suture 68.

The releasable suture clamp described herein provides a means for achieving and maintaining a desired tension of a suture without the use of knots. As such, procedures utilizing the disclosed suture clamp may require less time and money since, as should be appreciated, the knot tying process can be rather time consuming. Further, since the disclosed suture clamp is releasable, suture tension can be easily readjusted, as described herein, rather than the alternative of tying additional knots to increase tension and creating entirely new sutures to provide reduced tension. The releasable suture clamp described herein also has a relatively low profile and is capable of providing a more precise amount of tension as opposed to conventional knot tying procedures.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A suture anchor assembly, comprising:
a length of suture having an anchor attached to an end thereof; and
a releasable suture clamp disposed in a clamped configuration about the suture;
wherein the releasable suture clamp includes a plurality of independent stackable components, wherein each of the plurality of independent stackable components is rotatable about a common axis relative to an abutting one of the plurality of independent stackable components, wherein the common axis is transverse to opposing faces of the stackable components, wherein each of the stackable components has a first annular opening passing through the opposing faces, spaced from the common axis, and sized for receiving the suture therethrough;
wherein the releasable suture clamp has an unclamped configuration in which the first openings are aligned relative to an alignment axis and the clamped configuration in which the first openings are misaligned relative to the alignment axis, wherein the alignment axis is parallel to the common axis.

2. The suture anchor assembly of claim 1, further including:
a needle; and
a pusher slidably received in the needle;
wherein the anchor is received within a distal end of the needle and the suture extends outside of the needle.

3. The suture anchor assembly of claim 2, wherein the needle, the pusher, the anchor, and a segment of the suture are received in a blunt end holder.

4. The suture anchor assembly of claim 2, wherein the suture anchor assembly is received in a sterilized package.

5. A releasable suture clamp, comprising:
a plurality of independent stackable components, wherein each of the plurality of independent stackable components is rotatable about a common axis relative to an abutting one of the plurality of independent stackable components, wherein the common axis is transverse to opposing faces of the stackable components, wherein each of the stackable components has a first opening passing through the opposing faces, spaced from the common axis, and sized for receiving a suture therethrough;
wherein the releasable suture clamp has an unclamped configuration in which the first openings are aligned relative to an alignment axis and a clamped configuration in which the first openings are misaligned relative to the alignment axis, wherein the alignment axis is parallel to the common axis.

6. The releasable suture clamp of claim 5, wherein, in the clamped configuration, the first openings of abutting components are free from overlap; and
each of the first openings is an annular opening defined by a respective one of the stackable components.

7. The releasable suture clamp of claim 5, wherein a retaining pin is secured within second openings passing through the opposing faces of each of the stackable components to define the common axis.

8. The releasable suture clamp of claim 7, further including at least one spring member biasing the releasable suture clamp toward the clamped configuration.

9. The releasable suture clamp of claim 8, wherein the spring member is received within slots of the stackable components, wherein the slots of abutting components have a first overlap amount in the clamped configuration that is greater than a second overlap amount in the unclamped configuration.

10. The releasable suture clamp of claim 9, wherein each of the stackable components includes a lobe, wherein the lobes of abutting components are closer in proximity in the unclamped configuration than in the clamped configuration.

11. The releasable suture clamp of claim 10, further including a projection extending transversely from the lobe of at least one of the stackable components, wherein the projection restricts movement of the releasable suture clamp beyond a movement range defined by the clamped configuration and the unclamped configuration.

12. A method of clamping a suture with a releasable suture clamp, wherein the releasable suture clamp includes a plurality of independent stackable components, wherein the releasable suture clamp includes a plurality of independent stackable components that are each rotatable about a common axis relative to an abutting one of the plurality of independent stackable components, wherein the common axis is transverse to opposing faces of the stackable components, wherein each of the stackable components has a first opening passing through the opposing faces, spaced from the common axis, and sized for receiving a suture therethrough, the method comprising steps of:
moving the releasable suture clamp from a clamped configuration to an unclamped configuration by rotating the stackable components about the common axis such that the first openings are aligned relative to an alignment axis and define a linear path;
receiving the suture through the first openings of the stackable components along the linear path;
returning the releasable suture clamp from the unclamped configuration to the clamped configuration by rotating the stackable components about the common axis such that the first openings are misaligned relative to the alignment axis and define a serpentine path; and
restricting movement of the suture relative to the suture clamp by gripping the suture with edges defining the first openings and surfaces of the stackable components defining the serpentine path.

13. The method of claim 12, wherein the step of returning the releasable suture clamp to the clamped configuration includes rotating the stackable components such that the first openings of abutting components are free from overlap.

14. The method of claim 12, wherein the steps of moving the releasable suture clamp to the unclamped configuration and returning the releasable suture clamp to the clamped configuration include rotating the stackable components about a retaining pin secured within second openings passing through the opposing faces of each of the stackable components to define the common axis.

15. The method of claim 14, further including biasing the releasable suture clamp toward the clamped configuration using a spring member received within slots of the stackable components.

16. The method of claim 15, wherein the step of moving the releasable suture clamp to the unclamped configuration includes decreasing an overlap amount of the slots of abutting components, while the step of returning the releasable suture clamp to the clamped configuration includes increasing the overlap amount.

17. The method of claim 16, wherein the step of moving the releasable suture clamp to the unclamped configuration includes moving lobes of abutting components closer together, while the step of returning the releasable suture clamp to the clamped configuration includes moving the lobes of abutting components farther apart.

18. The method of claim 17, further including restricting movement of the releasable suture clamp beyond a movement range defined by the clamped configuration and the unclamped configuration using a projection extending transversely from the lobe of at least one of the stackable components.

19. The method of claim 12, further including:
passing the suture through a tissue layer; and
maintaining a first tension of the suture relative to the tissue layer using the clamped configuration of the releasable suture clamp.

20. The method of claim 19, further including:
moving the releasable suture clamp from the clamped configuration to the unclamped configuration by rotating the stackable components about the common axis such that the first openings define the linear path;
moving the suture along the linear path such that the suture has a second tension relative to the tissue layer that is different than the first tension;
returning the releasable suture clamp from the unclamped configuration to the clamped configuration by rotating the stackable components about the common axis such that the first openings define the serpentine path; and
maintaining the second tension by gripping the suture with the edges defining the first openings and surfaces of the stackable components defining the serpentine path.

* * * * *